(12) United States Patent
Bosshard et al.

(10) Patent No.: US 10,258,493 B2
(45) Date of Patent: Apr. 16, 2019

(54) KNEE ORTHOSIS FOR SUPPORT OF A KNEE JOINT

(71) Applicant: Ortho-Team AG, Bern (CH)

(72) Inventors: Adrian Bosshard, Bolligen (CH); Sandro Kohl, Bern (CH)

(73) Assignee: Ortho-Team AG, Bern (CH)

( * ) Notice: Subject to any disclaimer, the term of this patent is extended or adjusted under 35 U.S.C. 154(b) by 319 days.

(21) Appl. No.: 14/743,268

(22) Filed: Jun. 18, 2015

(65) Prior Publication Data

US 2015/0374530 A1 Dec. 31, 2015

(30) Foreign Application Priority Data

Jun. 25, 2014 (EP) .................................... 14173966

(51) Int. Cl.
*A61F 5/01* (2006.01)

(52) U.S. Cl.
CPC .... *A61F 5/0123* (2013.01); *A61F 2005/0132* (2013.01); *A61F 2005/0137* (2013.01);
(Continued)

(58) Field of Classification Search
CPC .... A61F 5/0123; A61F 5/0125; A61F 5/0113; A61F 2005/0132; A61F 2005/0134; A61F 2005/0137; A61F 2005/0146; A61F 2005/0148; A61F 2005/0155; A61F 2005/0167; A61F 2005/0179; A61F 2005/0181; A61F 2005/0141;
(Continued)

(56) References Cited

U.S. PATENT DOCUMENTS 4,523,585 A * 6/1985 Lamb .................. A61F 5/0123
602/16
4,961,416 A * 10/1990 Moore ................ A61F 5/0123
602/26
(Continued)

FOREIGN PATENT DOCUMENTS

DE 19811925 A1 10/1999
DE 10259751 A1 7/2004

OTHER PUBLICATIONS

Freely. Merriam Webster Online Dictionary, p. 1 definition 1d, https://www.merriam-webster.com/dictionary/freely.*
(Continued)

*Primary Examiner* — Alireza Nia
*Assistant Examiner* — Rachel A Berezik
(74) *Attorney, Agent, or Firm* — Alston & Bird LLP

(57) ABSTRACT

A knee orthosis (1) for support of a knee joint in the case of instability comprises a thigh portion (4), which is attachable on the thigh, and a lower leg portion (5), which is attachable on the lower leg, which lower leg portion (5) is provided with splint elements (12), which are connected in an articulated way, via articulation means (13), to hinge plates (14) attached on the thigh portion (4). The lower leg portion (5) has a lower half shell (9), which in the region remote from the knee is borne in the splint elements (12) in a way pivotable about a pivot axis (15). Via a longitudinally stable, flexible traction (17) the lower half shell (9) is pushed ventrally against the lower leg, the pressure increasing with bending of the knee. An optimal support of the knee joint is thereby achieved, especially when the cruciate ligaments are injured.

15 Claims, 7 Drawing Sheets

(52) U.S. Cl.
CPC ............... *A61F 2005/0155* (2013.01); *A61F 2005/0179* (2013.01)

(58) Field of Classification Search
CPC ...... A61F 2005/0144; A61F 2005/0151; A61F 2005/0153; A61F 2005/0169; A61F 5/01; A61F 5/0102; A61F 5/0111; A61F 5/0127; A61F 5/058; A61F 5/05825; A61F 5/05841; A61F 5/0585; A61F 2005/0139; A61F 2005/0158; A61F 2005/0165; A61F 2005/0172; A61F 2005/0174

See application file for complete search history.

(56) References Cited

U.S. PATENT DOCUMENTS

| | | | |
|---|---|---|---|
| 5,002,045 A | 3/1991 | Spademan | |
| 5,490,822 A * | 2/1996 | Biedermann | A61F 5/0123 602/16 |
| 7,309,322 B2 | 12/2007 | Albrecht et al. | |
| 2002/0133108 A1 * | 9/2002 | Jagodzinski | A61F 5/0123 602/16 |
| 2003/0093018 A1 * | 5/2003 | Albrecht | A61F 5/0123 602/16 |
| 2004/0127825 A1 * | 7/2004 | Castillo | A61F 5/0123 602/5 |
| 2006/0116616 A1 * | 6/2006 | Albrecht | A61F 5/0125 602/23 |
| 2006/0206045 A1 * | 9/2006 | Townsend | A61F 5/0125 602/26 |
| 2009/0287128 A1 * | 11/2009 | Ingimundarson | A61F 5/0111 602/27 |
| 2011/0098618 A1 | 4/2011 | Fleming | |
| 2013/0110020 A1 | 5/2013 | Ingimundarson et al. | |
| 2013/0245523 A1 * | 9/2013 | Romo | A61F 5/0125 602/16 |
| 2013/0296754 A1 * | 11/2013 | Campbell | A61F 5/0123 602/16 |
| 2013/0331754 A1 * | 12/2013 | Dunn | A61F 5/01 602/16 |
| 2014/0213948 A1 * | 7/2014 | Romo | A61F 5/0123 602/16 |

OTHER PUBLICATIONS

European Patent Office, European Search Report for Application No. EP 14173966, dated Dec. 1, 2014, 1 page, Germany.

* cited by examiner

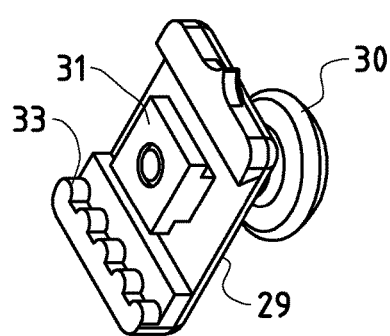
FIG. 9
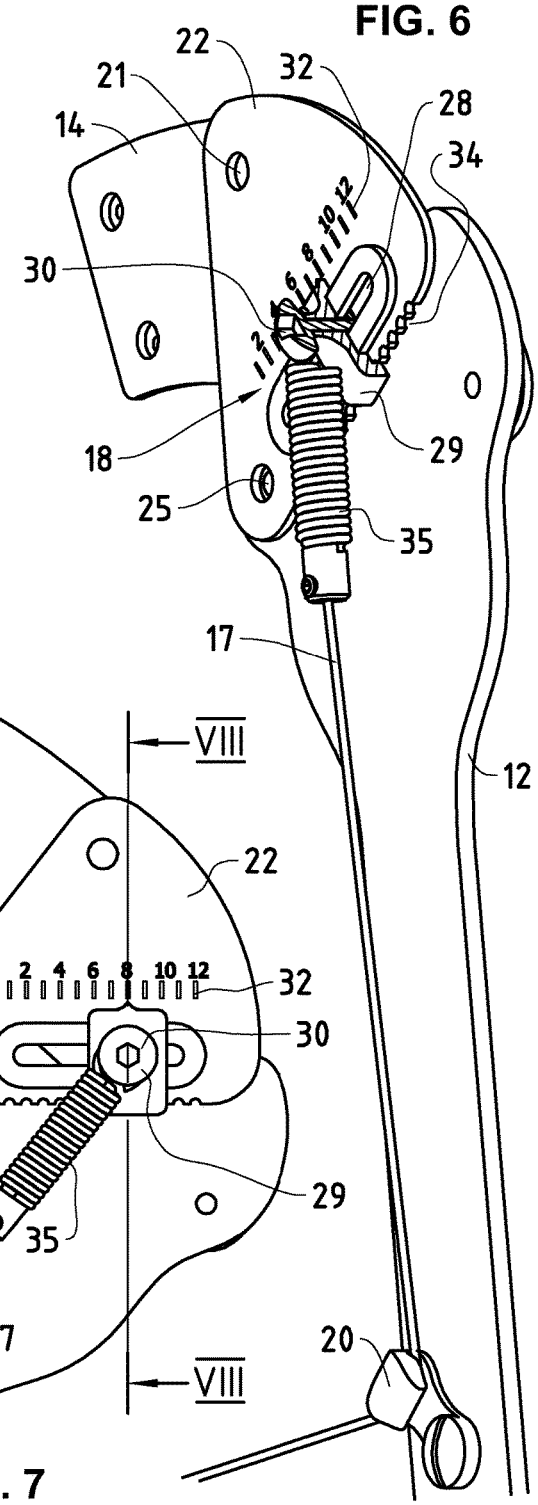
FIG. 6
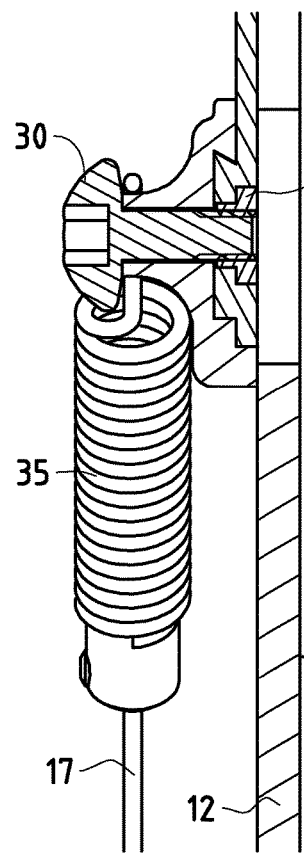
FIG. 8
FIG. 7

KNEE ORTHOSIS FOR SUPPORT OF A KNEE JOINT

CROSS-REFERENCE TO RELATED APPLICATIONS

This application claims priority to and the benefit of European Application No. 14173966.4, filed Jun. 25, 2014, the entire disclosure of which as is hereby incorporated by reference herein.

BACKGROUND

Related Field

The present invention relates to a knee orthosis for support of a knee joint in the case of instability, comprising a thigh portion, attachable on the thigh via fixing means, with an upper half shell and hinge plates fixed to the half shell, a lower leg portion, attachable to the lower leg via fixing means, with a lower half shell and splint elements attached laterally on the lower half shell, which splint elements are connected to the respective hinge plate via articulation means and in which splint elements, in the regions remote from the articulation means, the lower half shell is pivotably borne about a pivot axis and is pivotable toward the lower leg via adjustment means.

Related Art

Especially with knee instability owing to injury of the cruciate ligaments it is necessary for the knee joint to be supported in order to prevent in particular a defective position of the tibia to the femur. Knee orthoses are used for this purpose which give the knee joint the desired stability. It has been shown that with knee orthoses of this kind, especially with bent knee as occurs, for example, in a sitting position of the respective person, a displacement of the tibia to the femur nevertheless results. A displacement of this kind can have as a consequence an overstretching of the corresponding cruciate ligaments, which can occur both with a surgical as well as with a conservative treatment of the injury and should be avoided as much as possible.

The patent publication DE 102 59 751 A1 discloses a knee orthosis which is supposed to prevent such a displacement of the tibia to the femur. For this purpose this knee orthosis is designed in such a way that the lower half shell of the knee orthosis is pressed, via an adjustable spring pressure, toward the upper region of the lower leg in order to thereby counteract a movement of the tibia to the femur.

It has thereby been shown that this pressure against the upper region of the lower leg is not optimal. Thus, for example, this pressure can have the desired magnitude in the bent position of the knee, but in the stretched position of the knee this pressure is too great, which is disadvantageous.

BRIEF SUMMARY

The object of various embodiments of the present invention consists in creating a knee orthosis which does not have the above-mentioned drawbacks and with which the pressure in ventral or dorsal direction on the upper region of the lower leg is adapted depending upon the bending of the knee.

According to various embodiments of the invention this object is achieved in that the adjustment means are formed by at least one longitudinally stable, flexible traction element, whose one end region is held on a member of the articulation means pivotable with respect to the splint elements by means of a first holding device, whose other end region is held on the lower half shell by means of a second holding device and which longitudinally stable, flexible traction element is diverted between the first holding device and the second holding device about a diversion element mounted on the splint element.

Achieved with this design of the knee orthosis can be that the pressure on the upper region of the lower leg continuously increases during bending of the knee and thereby gives the knee the optimal stability in stretched and in any bent position. With this knee orthosis according to the invention the knee joint is supported in such a way that the corresponding cruciate ligament is kept in the anatomically correct position whereby a growth of the tendon stumps is also able to be achieved.

According to various embodiments, the articulation means are designed in each case as four joint system, and comprise a first member and a second member, which are each linked to the hinge plate and to the corresponding splint element. With this four joint system the rolling sliding movement of the knee joint can be reproduced, whereby the knee orthosis supports the knee joint in an optimal way.

The first holding device for holding the longitudinally stable, flexible traction element is mounted on the first member of the four joint system, whereby the swing distance which the lower half shell is supposed to carry out for exertion of the pressure on the upper region of the lower leg is optimally achievable.

According to various embodiments, the first holding device for holding the longitudinally stable, flexible traction element is adjustably mounted on the first member of the four joint system, whereby the swing distance of the lower half shell is adjustable and adaptable in an optimal way to the knee joint to be supported.

According to various embodiments, for adjusting the first holding device on the first member a slot-shaped recess is provided along which the first holding device is slidable and fixable in the set position, which makes possible simple manufacture and simple operation.

According to various embodiments, the first holding device is mounted in a sliding block which is slidable along the slot-shaped recess and is fixable through clamping means. Through this design there results a structurally simple solution for the setting possibility and good handling.

According to various embodiments, a scale is disposed along the slot-shaped recess, whereby the adjustment can be carried out in a simple and repeatable way.

Another non-limiting and advantageous embodiment of the invention consists in that at least one spring element is inserted in the longitudinally stable, flexible traction element. By means of this spring element pressure peaks which can act upon the upper region of the lower leg can be avoided, which improves the wearing comfort for this knee orthosis.

Another non-limiting advantageous embodiment of the invention consists in that the length of the longitudinally stable, flexible element is adjustable via a length adjustment device. This knee orthosis can thus be adapted in an optimal way to the respective patient, for example to differing muscle development.

According to various embodiments, the length adjustment device is integrated in the second holding device and is designed as rotatable knob whose shaft is borne in the lower half shell and about which the longitudinally stable, flexible element is able to be wound. A simple constructive design of this length adjustment device is thereby obtained, which is also simple to operate.

According to various embodiments, the first fixing means for the upper half shell and the second fixing means for the lower half shell are designed as bands with hook-and-loop fastener, whereby this knee orthosis can be fastened in an optimally adapted way to the leg of the person who requires support of the knee joint.

Another non-limiting and advantageous embodiment of the invention consists in that the longitudinally stable, flexible element is a cable, preferably made of fiber-reinforced synthetic material. Good sliding characteristics can thereby be obtained which are advantageous when the diversion element is provided with a sliding surface. In addition soiling is prevented.

Various embodiments of the invention will be explained more closely in the following, by way of example, with reference to the attached drawings.

BRIEF DESCRIPTION OF THE DRAWINGS

Figure 1:
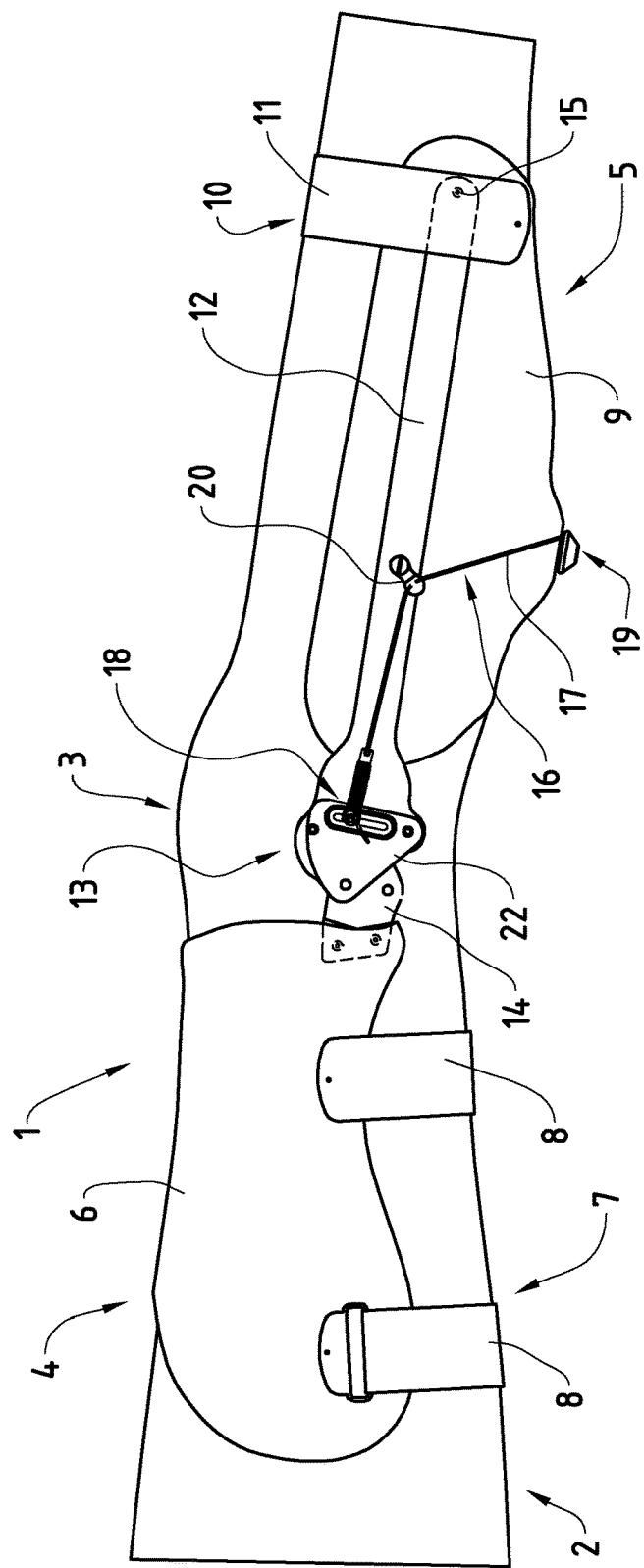
Figure 2:
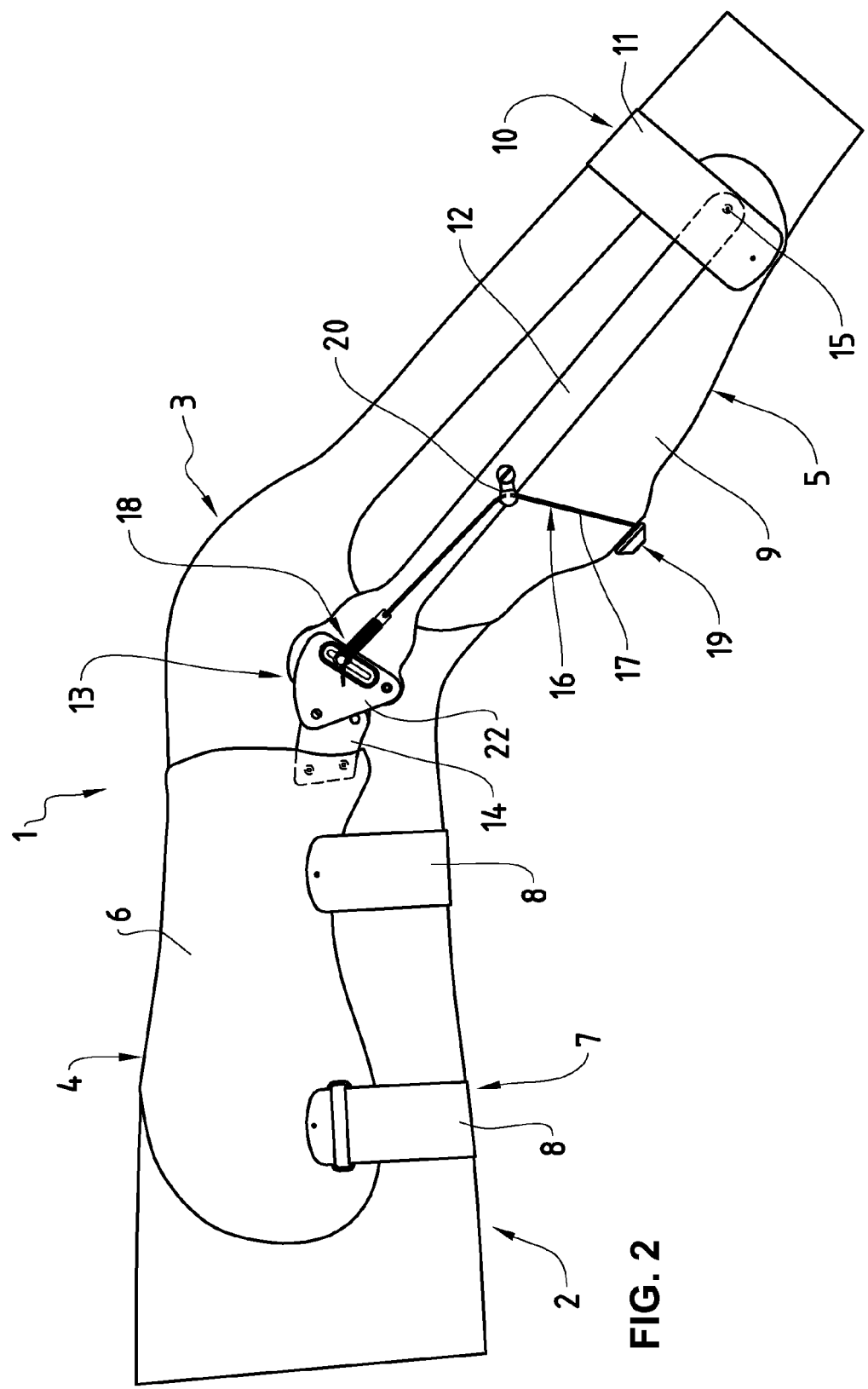
Figure 3:
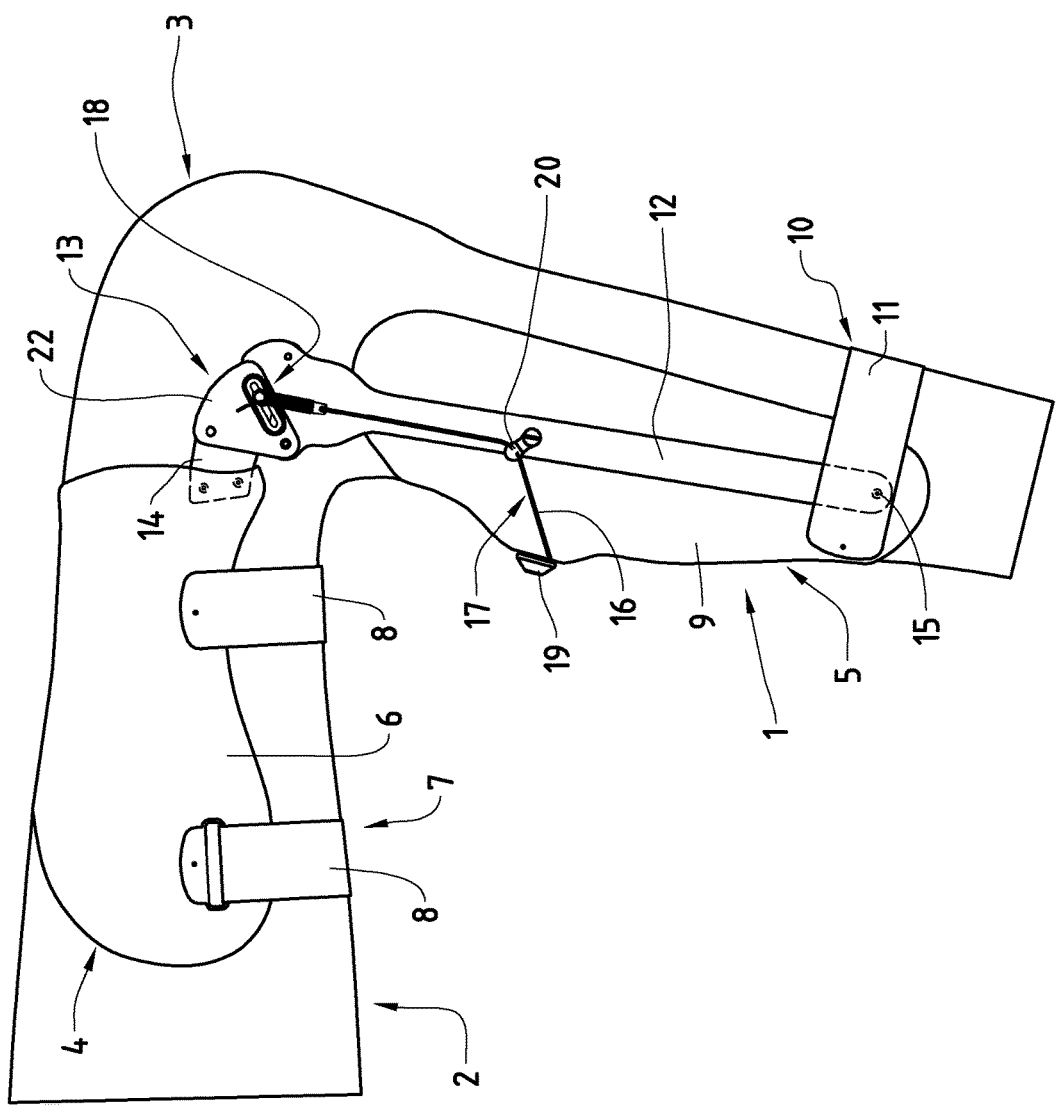
Figure 4:
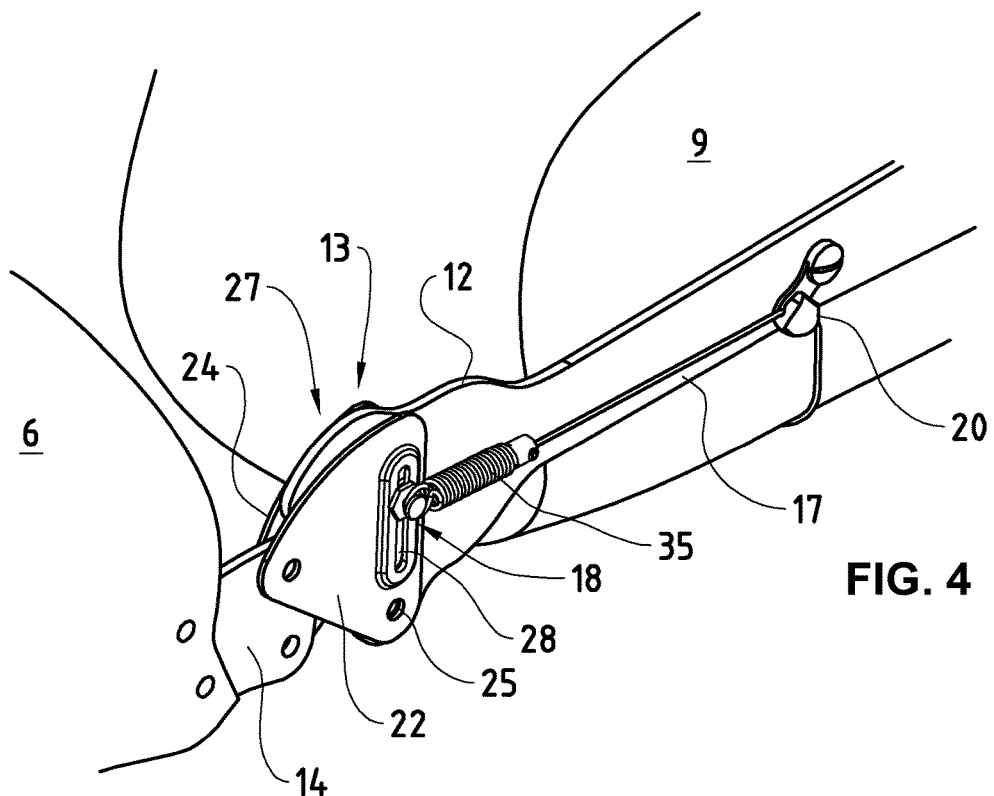
Figure 5:
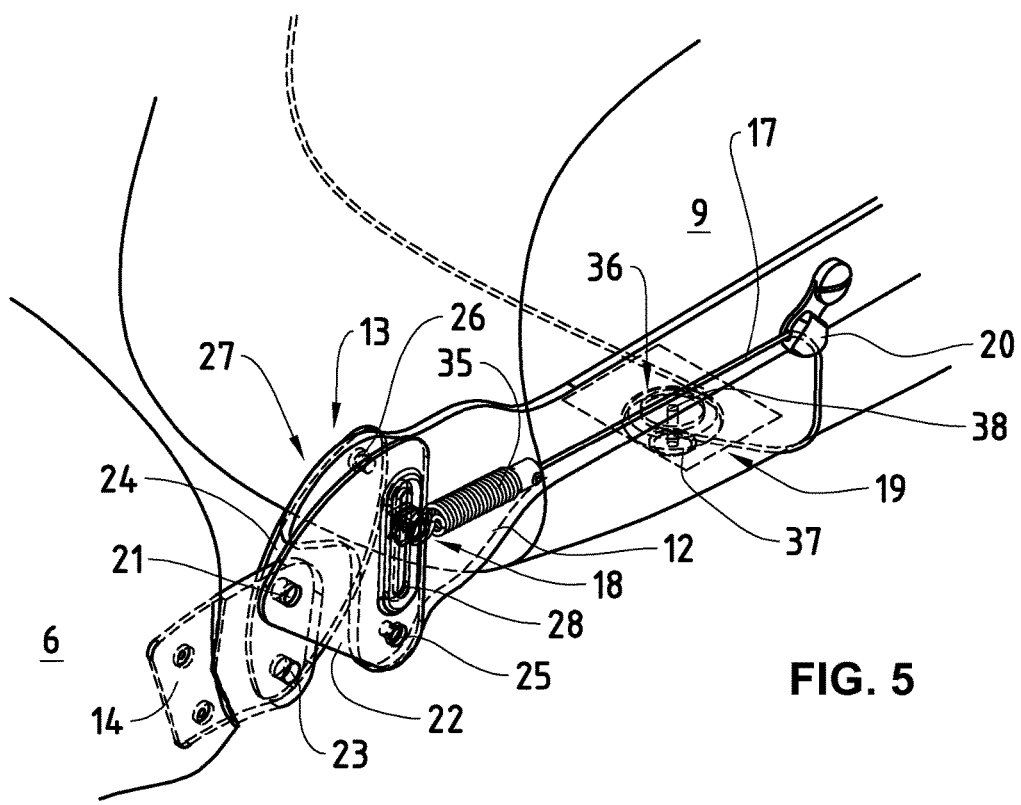
Figure 10:
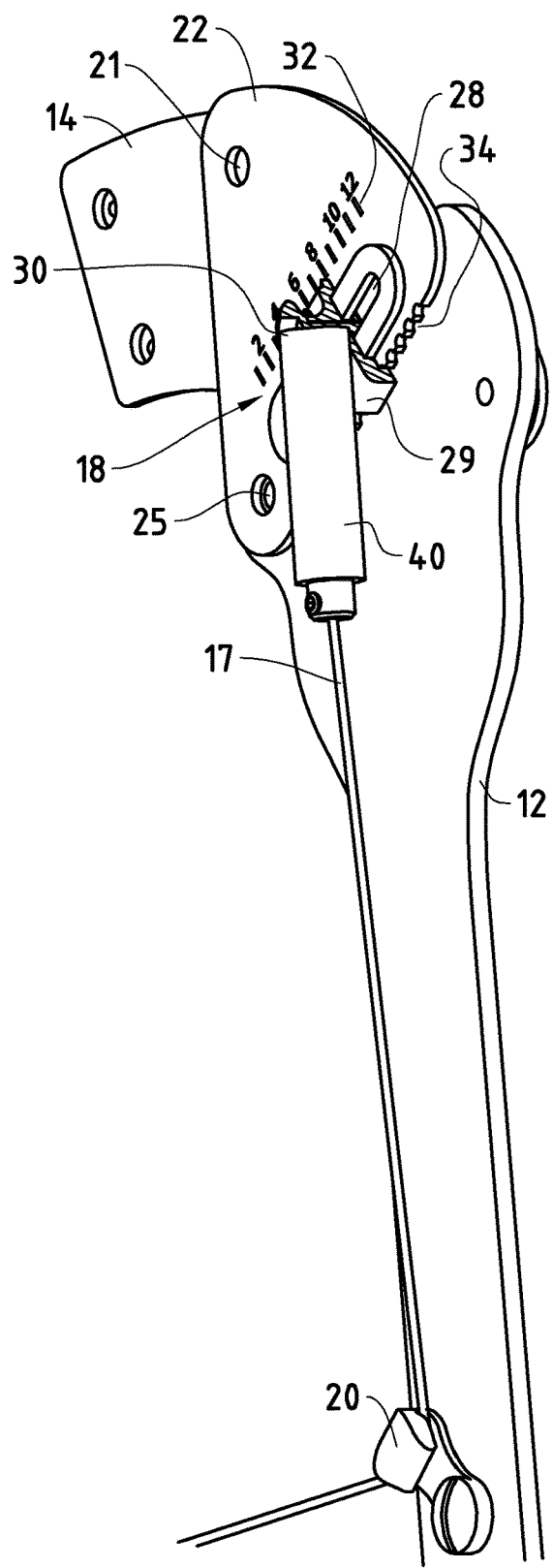

Having thus described the invention in general terms, reference will now be made to the accompanying drawings, which are not necessarily drawn to scale, and wherein:

FIG. 1 shows in a diagrammatic representation a knee orthosis according to the invention in the state of being attached to a leg, with knee stretched;

FIG. 2 shows the knee orthosis according to FIG. 1 with slightly bent knee;

FIG. 3 shows the knee orthosis according to FIG. 1 with strongly bent knee;

FIG. 4 shows in a spatial representation the four joint system of the knee orthosis with longitudinally stable, flexible traction element;

FIG. 5 shows in a spatial representation the four joint system according to FIG. 4, the non-visible lines being indicated as broken lines;

FIG. 6 shows in a spatial representation the adjustment device by means of which the first holding device can be adjusted in the first member of the four joint system;

FIG. 7 is a view of the adjustment device for the first holding device according to FIG. 6;

FIG. 8 is a sectional representation through the adjustment device for the first holding device along line VIII-VIII according to FIG. 7;

FIG. 9 shows in a spatial representation the view of a sliding block for the adjustment device; and FIG. 10 shows in a spatial representation a variant of the adjustment device according to the invention.

Figure 11:
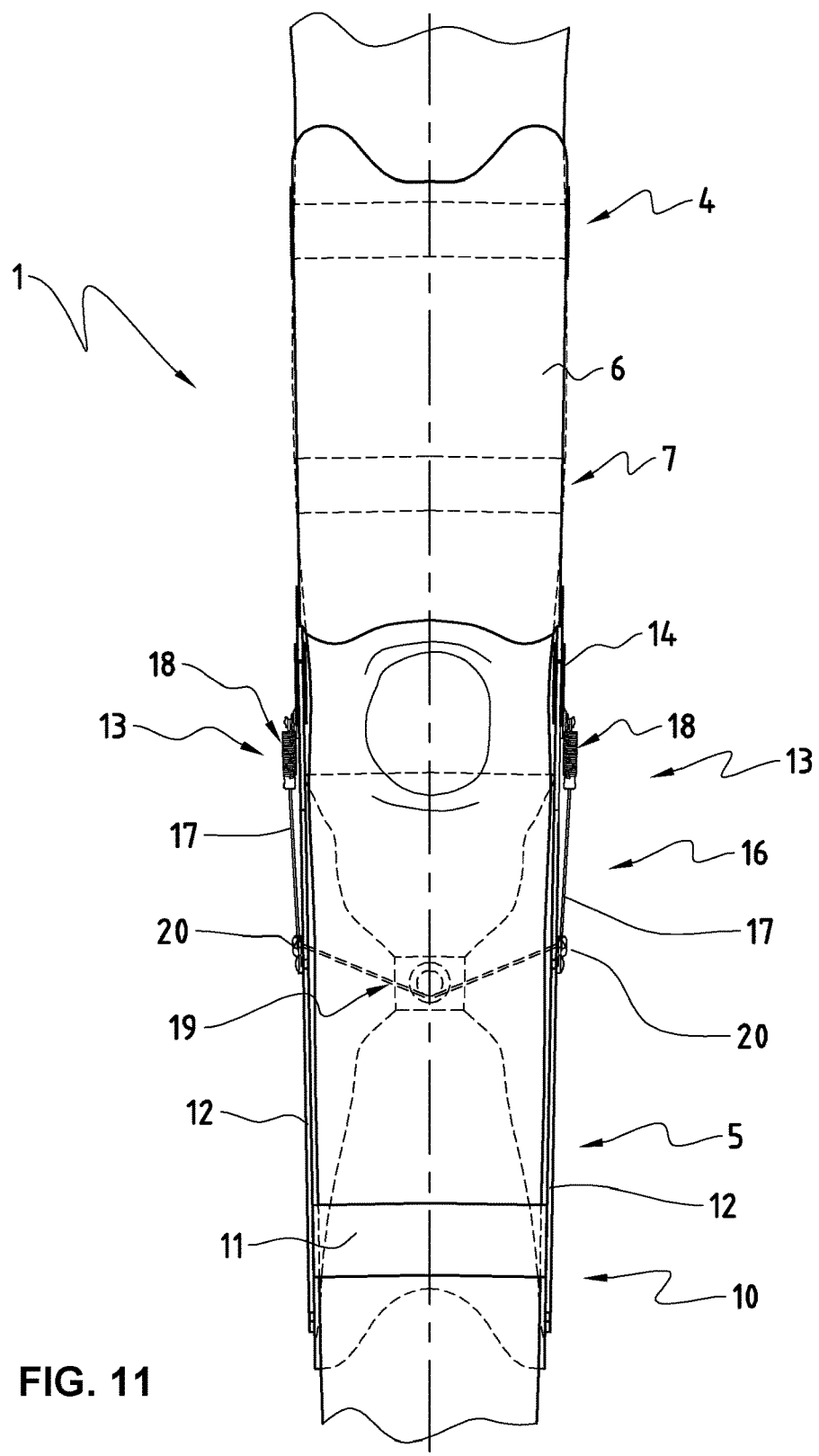

FIG. 11 shows the knee orthosis according to FIG. 1 from a front view relative to the knee, so as to illustrate both sides of the orthosis and its structural features.

DETAILED DESCRIPTION OF VARIOUS EMBODIMENTS

Various embodiments of the present invention will now be described more fully hereinafter with reference to the accompanying drawings, in which some, but not all embodiments of the invention are shown. Indeed, embodiments of the invention may be embodied in many different forms and should not be construed as limited to the embodiments set forth herein. Rather, these embodiments are provided so that this disclosure will satisfy applicable legal requirements. Unless otherwise defined, all technical and scientific terms used herein have the same meaning as commonly known and understood by one of ordinary skill in the art to which the invention relates. The term "or" is used herein in both the alternative and conjunctive sense, unless otherwise indicated. Like numbers refer to like elements throughout.

Still further, to facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

In FIGS. 1 to 3 and 11 a knee orthosis 1 according to the invention can be seen which is attached on the respective leg 2 of the knee 3 to be supported. FIGS. 1 and 11 hereby show the leg 2 with stretched knee 3, FIG. 2 shows the leg 2 with slightly bent knee 3, and FIG. 3 shows the leg 2 with strongly bent knee 3. The knee orthosis 1 hereby consists of a thigh portion 4 and a lower leg portion 5. The thigh portion 4 consists in a known way of an upper half shell 6, which can be fastened on the thigh in a known way from the front and fixed via first fixing means 7. These fixing means 7 can take in a known way the form of bands 8, which can be provided with hook-and-loop fasteners in a known way (not shown), whereby a simple and optimal attachment is made possible.

The lower leg portion 5 is formed by a lower half shell 9. This is placed on the lower leg from behind. Via a second fixing means 10, which is formed again in a known way by a band 11 with hook-and-loop fastener, the lower region of the lower half shell 9 is fixed to the lower leg.

Attached to both sides of the lower half shell 9 is one splint element 12 each, whose one end is connected in an articulated way to a hinge plate 14 via articulation means 13, which hinge plate 14 is fixed to the upper half shell. Via these articulation means 13, which will be described in detail later, the splint elements 12 are connected in an articulated way together with the lower half shell 9 and the upper half shell 6 in the region of the knee joint, which is imitated by the articulation means 13. The regions of the articulation means 13 remote from the splint elements 12 are pivotably borne on the lower half shell 9 and are pivotable about a pivot axis 15.

Via adjustment means 16 the lower half shell 9 can now be pushed about the pivot axis 15 in ventral direction against the upper portion of the lower leg. The adjustment means 16 hereby consist of a longitudinally stable, flexible traction element 17, whose one end region is held on a pivotable part of the articulation means 13 by means of a first holding device 18, as will be seen later. The other region of this longitudinally stable, flexible traction element 17 is held on the lower half shell 9 by means of a second holding device 19. Attached on the respective splint element 12, at approximately the height of the second holding device 19, is a diversion element 20, about which the longitudinally stable, flexible traction element 17 is diverted in a sliding way between the first holding device 18 and the second holding device 19. The longitudinally stable, flexible traction element 17 can thereby be designed as a cable, made of synthetic material with a smooth surface, if necessary reinforced with fibers, so that the friction is able to be kept as minimal as possible in the diversion element 20. Of course other known and suitable longitudinally stable, flexible traction elements 17 are also conceivable and usable. In certain embodiments, as evident from FIGS. 6-8, the longitudinally stable, flexible traction elements 17 is defined by a cable having a spring element 35 attached to one end thereof.

Shown in FIGS. 4 and 5 are the articulation means 13, which are designed as four joint system 27. This four joint system 27 comprises the hinge plate 14, which is attached to the upper half shell 6. Via a first hinge bearing 21 a first member 22 is pivotably connected to the hinge plate 14. Via a second hinge bearing 23, which is also disposed on the hinge plate 14, a second member 24 is pivotably connected to the hinge plate 14. The first member 22 is pivotably connected to the upper part of the splint element 12 via a third hinge bearing 25, while via a fourth hinge bearing 26 the second member 24 is also pivotably connected to the upper region of the splint element 12. As can be seen from FIGS. 4 and 5, the first member 22 and the second member 24 intersect. By means of this known four joint system configuration, the rolling sliding movement of the knee joint is reproduced in an optimal way.

As can also be seen from FIG. 4 and FIG. 5, the first holding device 18 for the longitudinally stable, flexible traction element 17 is disposed on the first member 22 of this four joint system 27. With bending of the knee orthosis the first member 22 is pivoted with respect to the splint element 12 slightly clockwise about the third hinge bearing 25, whereby a pull is exerted on the longitudinally stable, flexible traction element 17, as will be described in the following.

In FIG. 1 the knee and thus the knee orthosis are in stretched position. Via the longitudinally stable, flexible element 17 the lower half shell assumes with respect to the splint element 12 a position shown in FIG. 1. With a slight bending of the knee joint and thus of the knee orthosis 1 the longitudinally stable, flexible traction element 17 is pulled in the direction of the thigh by means of the configuration of the first holding device 18, as has been described in the foregoing. Via the diversion element 20 the longitudinally stable, flexible traction element 17 pulls the lower half shell 9, pivotably about the pivot axis 15, in ventral direction against the lower leg. The lower leg or respectively the tibia is thus also pushed in ventral direction with respect to the femur, which leads to relief of the posterior cruciate ligament.

With a strong bending of the knee joint and of the knee orthosis, through the further pivoting of the first member 22 with respect to the splint element 12, the lower half shell 9 is pushed even more forcefully about the pivot axis 15 against the lower leg, which with a strongly bent knee results in an optimal relief of the posterior cruciate ligament. With stretching of the knee the pressure of the lower half shell 9 on the lower leg decreases again and the starting position is again reached.

As can be seen in particular from FIGS. 4 and 5, the respective first holding device 18 is disposed in an adjustable way on the first member 22 of the four joint system 27. A slot-shaped recess 28 is provided for this purpose on the first member 22, along which recess the first holding device 18 is displaceable and fixable in the adjusted position, as will be described in the following. With reference also to FIGS. 6-8, it may be understood that the spring element 35 has a longitudinal spring axis along which the spring element extends. The slot-shaped recess 28 also have a longitudinal slot axis, and these two components are always positioned such that the longitudinal a lot axis is not parallel to the longitudinal spring axis. This permits selective relative displacement of each component, as described elsewhere herein.

As can be seen from FIGS. 6 to 9, this first holding device 18 consists of a sliding block 29, which is displaceable along the slot-shaped recess 28. In a known way attached to this sliding block 29 is a clamping screw 30 which is screwed into a clamping element 31. Via the clamping screw 30 and the clamping element 31 the sliding block 29 can be fixed in the adjusted position in the slot-shaped recess 28. Disposed on the first member 22 along the slot-shaped recess 28 is a scale 32. By means of this scale 32 the sliding block 29 can be set in the desired position and in a repeatable way. In addition teeth 33 can be provided on this sliding block 29, which are able to engage in a corresponding toothing 34 which is provided on the first member 22 along the slot-shaped recess 28, which facilitates the setting and improves the fixation. The longitudinally stable, flexible traction element 17 can be hooked on the sliding block 29. By means of this adjustment capability the pivot path of the first holding device 18 about the third hinge bearing 25 can be increased or decreased, whereby the pivot path of the lower half shell 9 is increased or decreased accordingly. The pressure which the lower half shell 9 is supposed to exert on the lower leg in ventral direction can be thereby increased or decreased; an adaptation to the body constellation is thereby easily possible, depending upon how the musculature of the wearer is developed, for example.

As can be seen in particular from FIGS. 4 to 8, inserted on the end region or at one end of the longitudinally stable, flexible traction element 17, which is held in the first holding device 18, is a spring element 35, which is designed in the present embodiment example as a spiral spring. With this spring element 35 a certain elasticity of the longitudinally stable, flexible traction element 17 is obtained. Excessive pressures on the lower leg can thereby be cushioned. By providing a marking, a maximal range of spring can be established, with the surpassing of which the tractive force of the spring element would be too great. The spring elements are replaceable. At any one time spring elements with spring characteristics corresponding to the desired requirements can be used. As evident from FIGS. 6-8 in particular, the spring element 35 may have a distal end connected to one end of the cable described elsewhere herein; the opposing proximal end of the spring element may be attached to or otherwise held on the articulation means 13.

As can be seen in particular from FIG. 5, the second holding device 19 for the longitudinally stable, flexible traction element 17 on the lower half shell 9 is provided with a length adjustment device 36. This length adjustment device 36 can be formed by a rotatable knob 37, whose shaft 38 is borne in the lower half shell 9, and about which the two ends of the longitudinally stable, flexible traction element 17 are able to be wound. Via this length adjustment device 36 the basic position of the lower half shell 9 can be set and can be adapted to the body constellation of the wearer of this knee orthosis, for example depending on how the musculature is developed. Such length adjustment devices are known in diverse ways, which is why they are not shown and described more closely here. Of course other known adjustment devices are also conceivable which are suitable for such application.

FIG. 10 shows a variant of the adjustment device as described above. In this variant a marking sleeve 40 at least partially covers the spring element 35. The sleeve 40 has a determined length in direction of the axis of the spring element 35. Therefore the lower edge of the, from which the flexible traction element 17 extends, serves as reference indication for the tension of the spring element 35. In responds to a stronger or lesser traction of the spring element 35 the lower part of the spring element 35 extends more or less relative to the sleeve 40. The extending length may serve as indication of tension of the flexible traction element 17. Also small indication signs may be printed on the flexible traction element 17 to help identifying a difference in the extending length. Such indication sleeve is an advantageous aid in adjusting the knee orthosis for a patient on its own. Also the indication is helpful in addition to the length adjustment device 36. The sleeve can provide a marking as mentioned above, so that a maximal range of spring can be established, with the surpassing of which the tractive force of the spring element would be too great.

With an injury of the anterior cruciate ligament, the upper half shell 6 and lower half shell 9 of the knee orthosis 1 according to the invention can be placed in the knee orthosis 1 in such a way that the upper half shell 6 can be placed on the thigh from behind, while the lower half shell 9 can be placed on the lower leg from the front. The diversion of the longitudinally stable, flexible traction element 17 takes place then in ventral direction. With bending of the knee the lower half shell 9 is thus pushed about the pivot axis 15 dorsally toward the knee joint. The tibia is thereby also pushed in dorsal direction with respect to the femur, which leads to relief of the anterior cruciate ligament.

With this knee orthosis according to the invention an optimal support of the knee joint can be achieved, in particular when there is an injury of the posterior or anterior cruciate ligament. By means of this knee orthosis the knee joint is supported in an optimal way in particular when it is bent.

The invention is not limited to the above-described embodiments and many modifications are possible within the scope of the following claims. Indeed, a person of ordinary skill in the art would be able to use the information contained in the preceding text to modify various embodiments of the invention in ways that are not literally described, but are nevertheless encompassed by the attached claims, for they accomplish substantially the same functions to reach substantially the same results. Therefore, it is to be understood that the invention is not limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. Knee orthosis for support of a knee joint in the case of instability, said knee orthosis comprising:
   a thigh portion (4), attachable on a thigh via first fixing means (7), with an upper half shell (6) and hinge plates (14) each attached laterally to the upper half shell (6),
   a lower leg portion (5), attachable on a lower leg via second fixing means (10), with a lower half shell (9) and splint elements (12) each attached laterally on the lower half shell (9),
   wherein:
      each of said splint elements (12) is connected via articulation means (13) to a respective one of the hinge plates (14);
      in each of said splint elements (12), in the regions remote from the articulation means (13), said lower half shell (9) is pivotably borne about a pivot axis (15) and is pivotable, via adjustment means (16), toward the lower leg;
      the adjustment means (16) comprises at least one longitudinally stable, flexible traction element (17) that includes a cable and at least one spring element (35), the cable having a first end and a second end opposite the first end, the at least one spring element (35) having a proximal end and a distal end opposite the proximal end, the distal end of the at least one spring element (35) being directly connected to the first end of the cable, such that the at least one spring element (35) extends beyond the first end of the cable; and such that a central longitudinal axis of the first end of the cable is aligned coaxially with a central longitudinal axis of the spring element;
      the proximal end of the at least one spring element (35) is held on a member (22; 24) of the articulation means (13) and pivotable with respect to each of the splint elements (12) by means of a first holding device (18);
      the second end of the at least one longitudinally stable, flexible traction element (17) is held on the lower half shell (9) by means of a second holding device (19);
      and
      a portion of the cable of the at least one longitudinally stable, flexible traction element (17) intermediate the first and second ends thereof is diverted between the first holding device (18) and the second holding device (19), said diversion occurring about a diversion element (20) mounted on each of the splint elements (12), the diverted portion of the at least one longitudinally stable, flexible traction element (17) sliding about said diversion element (20).

2. Knee orthosis for support of a knee joint according to claim 1, wherein:
   the articulation means (13) is a four joint system (27) having a first member (22) and a second member (24); and
   the first member (22) and the second member (24) are each linked to a respective one of the hinge plates (14) and to a corresponding one of the splint elements (12).

3. Knee orthosis for support of a knee joint according to claim 2, wherein the first holding device (18) is mounted for holding the at least one longitudinally stable, flexible traction element (17) on the first member (22) of the four joint system (27).

4. Knee orthosis for support of a knee joint according to claim 3, wherein the first holding device (18) for holding the at least one longitudinally stable, flexible traction element (17) is adjustably mounted on the first member (22) of the four joint system (27).

5. Knee orthosis for support of a knee joint according to claim 3, wherein for adjusting the first holding device (18) on the first member (22) a slot-shaped recess (28) is provided along which the first holding device (18) is slidable and fixable in a set position.

6. Knee orthosis for support of a knee joint according to claim 5, wherein the first holding device (18) is mounted in a sliding block (29) which is slidable along the slot-shaped recess (28) and is fixable through clamping means (30, 31).

7. Knee orthosis for support of a knee joint according to claim 5, wherein a scale (32) is disposed along the slot-shaped recess (28).

8. Knee orthosis for support of a knee joint according to claim 1, wherein a length of the at least one longitudinally stable, flexible traction element is adjustable via a length adjustment device (36).

9. Knee orthosis for support of a knee joint according to claim 8, wherein the length adjustment device (36) is integrated in the second holding device (19) and is designed as a rotatable knob (37) whose shaft (38) is borne in the lower half shell (9) and about which the at least one longitudinally stable, flexible traction element (17) is able to be wound.

10. Knee orthosis for support of a knee joint according to claim 1, wherein the first fixing means (7) for the upper half shell (6) and the second fixing means (10) for the lower half shell (9) are bands (8, 11) with hook-and-loop fasteners.

11. Knee orthosis for support of a knee joint according to claim 1, wherein a marking sleeve (40) at least partially covers the spring element (35) in an axial direction of the spring element.

12. Knee orthosis for support of a knee joint according to claim 1, wherein:
- the diversion element (20) comprises a sliding surface, and
- the diverted portion of the cable of the at least one longitudinally stable, flexible traction element (17) slides along the sliding surface about said diversion element (20).

13. Knee orthosis for support of a knee joint according to claim 1, wherein:
- the member (22; 24) of the articulation means (13) includes a slot-shaped recess (28);
- the first holding device (18) includes a sliding block (29), displaceable along the slot-shaped recess (28); and
- the proximal end of the at least one spring element (35) is held on the member (22; 24) via the sliding block (29).

14. Knee orthosis for support of a knee joint according to claim 13, wherein:
- the first holding device (18) further includes clamping means (30, 31);
- the sliding block (29) is selectively fixable via the clamping means at any one of a plurality of positions along the slot-shaped recess (28).

15. Knee orthosis for support of a knee joint according to claim 13, wherein:
- the at least one spring element (35) has a longitudinal spring axis along which the spring element extends; and
- the slot-shaped recess (28) has a longitudinal slot axis, the longitudinal slot axis being non-parallel to the longitudinal spring axis.

* * * * *